United States Patent [19]

Bouami et al.

[11] Patent Number: 4,763,528

[45] Date of Patent: Aug. 16, 1988

[54] NON-DESTRUCTIVE METHOD FOR DETERMINING AT LEAST ONE POINT OF A CRACK FRONT IN A PART AND AN APPARATUS FOR THE IMPLEMENTATION OF THE METHOD

[75] Inventors: Driss Bouami, Chatenay Malabry; Daniel De Vadder, Verrieres Le Buisson, both of France

[73] Assignee: Ecole Centrale Des Arts Et Manufactures, Chatenay Malabry Cedex, France

[21] Appl. No.: 2,758

[22] PCT Filed: Apr. 15, 1986

[86] PCT No.: PCT/FR86/00124

§ 371 Date: Dec. 5, 1986

§ 102(e) Date: Dec. 5, 1986

[87] PCT Pub. No.: WO86/06169

PCT Pub. Date: Oct. 23, 1986

[30] Foreign Application Priority Data

Apr. 16, 1985 [FR] France .................................. 85 05696

[51] Int. Cl.[4] ........................................... G01N 19/08
[52] U.S. Cl. ............................................ 73/799; 73/577
[58] Field of Search .......................... 73/799, 577, 627

[56] References Cited

U.S. PATENT DOCUMENTS

| 3,332,278 | 7/1967 | Wood. | |
|---|---|---|---|
| 4,292,848 | 10/1981 | Rainey | 73/602 |
| 4,441,369 | 4/1984 | Lessard et al. | 73/602 |

OTHER PUBLICATIONS

Nakazawa et al., "Proceedings of 4th Symposium on Ultrasonic Electronics", Japanese Journal of Applied Physics, vol. 23, suppl. 23-1.

Nakazawa, H. et al., Ultrasonic Monitoring . . . Materials, Japanese Journal of Applied Physics, vol. 23, Suppl. 23-1, 1983, pp. 12-16.

Andrews, E. H. et al., An Ultrasonic Technique . . . Velocities, Journal of Materials Science, No. 8, 1971, pp. 1093-1099.

Primary Examiner—Jerry W. Myracle
Attorney, Agent, or Firm—Cushman, Darby & Cushman

[57] ABSTRACT

The device concerns a method for detecting the position of at least one point of the crack front within a part (4) subjected to fatique stresses or to a ductile rupture. An ultrasonic beam is used focused in the plane P of the crack growth; the axis of this beam forms an angle comprised between 50° and 80° with P. The beam is displaced until the echo passes through a maximum, in which case the focusing is situated at the tip of the crack in the plane of displacement. The invention also concerns a device for the implementation of the method.

19 Claims, 1 Drawing Sheet

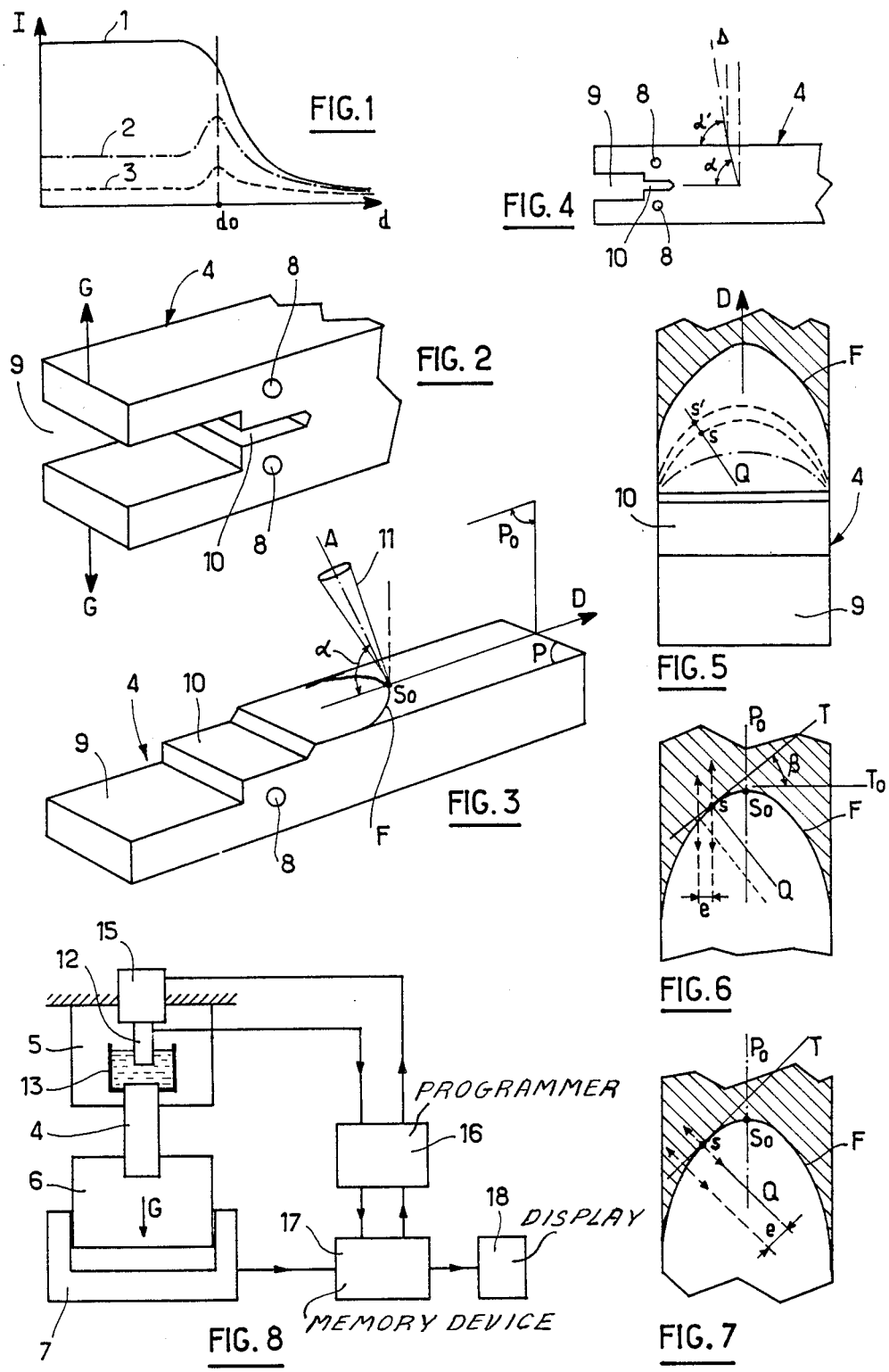

NON-DESTRUCTIVE METHOD FOR DETERMINING AT LEAST ONE POINT OF A CRACK FRONT IN A PART AND AN APPARATUS FOR THE IMPLEMENTATION OF THE METHOD

The present invention relates to a method for detecting the shape and/or the position of a crack front within a part, especially a metallic one, subjected to stresses which cause its fracture or ductile rupture.

The importance of being able to track the evolution of the crack in a test piece under fatigue conditions or monotonic loading is well known. The definition of the shape of the crack front and the determination of its position at any given time and of its growth rate is useful in the assessment of the mechanical properties of the test-piece material. In particular, the toughness of the material that is to say, its resistance to sudden crack growth can be deduced from the calculation of the Rice integral, which is the (line) integral of the energy density over a closed circuit around the crack (see in this respect the article by J. R. Rice in "Fracture" Vol. II p. 191 ed. Leibowitz 1968, Academic Press). It is therefore important to be able to monitor with precision the shape and the instantaneous position of the crack front in a test piece.

Several methods are used for this determination including the so-called multi-specimen method: according to this method, several specimens are used which are exposed to the desired stress levels for a longer or shorter time, and once the stressing of the test piece has been stopped, the cracked region is marked, usually by oxidation after which the specimen is broken to allow the observation and measurement of the position and shape of the crack front. This destructive testing technique has essentially two disadvantages: on the one hand, it requires the use of a large number of specimens which leads to increases in the cost of the study and the necessary time; and on the other hand, one is confronted with variations between the structures of the different test-pieces because of the number of specimens used.

It has been suggested that the progression of crack growth fronts could be studied using non-destructive methods which are based either on the observation of the growth of the crack at the edge of the part, or on some method, in particular mechanical or electrical, allowing a rectilinear line to be positioned which constitutes the median line of the real crack front. The disadvantage with these methods is that it is not possible to determine either the exact shape of the crack front or the development of this shape in the course of the crack formation, so that it is necessary to make a hypothesis on the shape of the curves corresponding to the crack front in order to be able to calculate the elements serving for the toughness determination of the material. These non-destructive methods thus have the drawback of being imprecise by reason of the lack of the determination of the shape and exact position of the crack front.

Among the non-destructive methods of the type described above, the use of an ultrasonic generator "transducer" has been suggested (see in the respect the article "An Ultrasonic Crack Growth Monitor" by W. G. Clark and L. J. Ceschini, Materials Evaluation, August 1969, pages 180 to 184). According to this method, an ultrasonic beam generated from a flat "transducer" is injected into the test piece subjected to cracking; the axis of the diverging beam is disposed perpendicularly to the fracture plane and the displacement of the crack front with respect to the axis of the ultrasonic beam entails a modification in the reception amplitude. The principle of the method is to displace the "transducer" in such a way as to maintain a constant reception and it is then assumed that the displacement of the "transducer" is equal to the displacement of the crack front. In fact, this method would only give an accurate displacement of the crack front if the latter were to have a constant shape throughout the displacement in the material, which is not the case. Moreover this method permits the definition of neither the effective shape of the crack front, nor the precise position of the tip or end of the crack.

The object of the present invention is the proosal of a non-destructive method allowing the definition of the progress of the crack front or of the ductile rupture front, and of the form of this front in a part or test-piece, a metallic one in particular, exposed to cyclic fatigue stresses or monotonic loading. The invention uses a "transducer" ultrasound generator and uses an edge-effect phenomenon which has already been described. In effect, it is known (see the publication of De Vadder, Azou, Bastien, Saglio—"Detection of large planar misoriented defects using focused ultrasonic transducers", 8th World Conference on Non-Destructive Testing—Cannas, September 1976) that if a focused ultrasonic beam is directed towards a sharp edged quasi-planar defect inside a part, with the focusing being ensured in the plane of the defect, and if the plane of the defect is not perpendicular to the axis of the ultrasonic beam, then in this case the echo sensed by the receiver is maximised when the beam strikes the edge of the defect. According to the invention, it has been suggested that the edge effect mentioned above be used to define the crack front in a part which is stressed. It should be noted that the edge effect produced with a convergent ultrasonic beam has until now only been used to define the edges of a defect inside a part, whereas on the contrary, the progress of a fatigue crack inside a test piece has only been studied using a divergent ultrasonic beam in which the axis was perpendicular to the plane of the crack. According to the invention, a convergent ultrasonic beam is used to track the position of the crack front and its possible displacement with respect to time. Hitherto, such a beam had only been used to monitor a static defect, whereas the invention describes the use of the edge effect for the continuous tracking of a growing crack.

The object of the present invention is thereforea method for detecting the position of at least one point of the crack front within a part comprising substantially in a plane P a crack or ductile rupture on either side of a median plane $P_o$ perpendicular to P; the said method consisting in sending an incident beam of ultrasound along an axis A over the crack plane P, to register the intensity of the echo produced by diffraction over P on a receiving device in order to deduce therefrom an evaluation of the position of the crack tip characterised in that;

if the plane P is not defined in a sufficiently precise manner, the said plane P is determined in the known way, by measuring the transit time of the diffracted ultrasonic wave;

an incident beam of ultrasounds is subsequently used, which is focused in such a manner that the plane P intersects its useful zone making an angle $\alpha$ with its axis A comprised between approximately 10° and 80°;

the said beam is oriented so that the plane Q normal to P passing through A should be substantially perpendicular to the crack front;

the axis A is displaced towards the crack front until the echo registered is maximised, the point S, which is the intersection of A and P being the tip of the crack in the plane Q.

In a preferred mode of implentation of the method according to the invention, the angle $\alpha$ is comprised between 60° and 75°; the detection begins in bringing the plane Q to be substantially identical with $P_o$ to determine the crack tip $S_o$ situated in $P_o$.

If it is desired to follow the displacement of the crack tip in a direction D with respect to time, an alternate translation of the ultrasonic beam axis A is secured parallel to the direction D of the crack growth, on either side of the position which has given rise to the location of S and when a significant variation is found in the position of axis A of the incident beam for the maximum echo, the new position of the crack tip S' is marked and S is replaced by S' as the reference point for the alternate translation of A.

If, on the other hand, it is desired to define all or part of the shape of the crack front in the part being examined, having determined the crack tip $S_o$ situated in $P_o$ the axis A of the beam is displaced perpendicularly to the plane $P_o$ to bring it into a plane $P_1$ parallel to $P_o$, the axis A is then displaced parallel to $P_o$ until the maximum in the echo is registered in order to position the crack tip in $P_1$ and so on, step by step until the tangent T to the crack tip thus defined should then in the sequencemake a predetermined angle $\beta$ with its initial position which is comprised between approximately 5° and 30°; if one wishes to continue with the definition of the crack front, the axis A is reoriented so that the plane Q should in the sequence make an angle of less than 2$\beta$ with its original position preferably comprised between $\beta$ and 2$\beta$, and better still, approximating to $\beta$, and the axis A is again subjected to a series of sequences formed by a displacement in view of the detection of a maximum in the echo and a transverse shift in relation to the said displacement. In this type of application, it is preferred that the angle $\beta$ be comprised between 10° and 20°.

According to a first variant of the implementation of the invention designed to define the shape of the crack front and/or to follow the displacement of the crack front, after the reorientation of the axis A, the said axis is displaced parallel to $P_o$ and it is shifted transversely and perpendicularly to $P_o$; in another variant, after the reorientation of the axis A, A is displaced parallel to the intersection of P with the plane Q and it is shifted transversely and perpendicularly to Q.

The object of the present invention is also a device allowing the process as defined above to be implemented.

This device entails means for fixing the part being studied, a means for subjecting the said part to mechanical forces with the result of producing a crack or ductile rupture in plane P of the part, at least one "transducer" ultrasound generator capable of producing a focused incident beam and at least one receiver capable of registering the intensity of the echo originating from a zone in the part, characterised in that the "transducer" provides a focused incident beam of ultrasound such that the plane P intersects its useful zone and makes an angle $\alpha$ comprised between approximately 10° and 80° with its axis A and that the device provides a means for orientating the axis A around a perpendicular axis P, means for shifting the axis with a translation parallel to a first direction of the plane P, and means for a transverse shift by a translation of the axis A parallel to a second direction of the plane P.

In a preferred mode of embodiment of the device according to the invention, the angle $\alpha$ is comprised between 60° and 75°; the means for shifting the axis A in translation is subjected to a means of control which makes it possible to ensure either a continuous translation until a receiver registers a maximum echo followed by a return movement, that is to say an alternating translation about a reference point, for which the receiver registers a maximum echo, with the said point of reference being memorised with respect to time; the means for the transverse shift of the axis A produce a translation of the said axis in a second direction which is perpendicular to the first direction; the means for a translational displacement of axis A ensure a translation along a single first direction positioned in relation to the means for fixing the part; the means for orientating and displacing or shifting the axis A, are,as from the detection of the crack tip $S_o$ siutated in the median plane $P_o$ on either side of which the crack front is lying, automatically controlled by a programmer, the geometrical position of all or part of the crack front and its displacement with respect to time being memorised by computer with a view to a digital or graphical read out.

The transducer, which is used in the application of the invention, can be any one of the known types. In particular, it should be possible to use a planar "transducer" focused by a plano-concave lens or a "transducer" in which the end face is concave or several elementary "transducers" which are electronically focused at emission or reception. In the latter case, the translations and orientations of the beam can be ensured electronically, without displacements of the transducers by known means. To ensure the connection between the ultrasonic generator "transducer" and the part to be investigated, a connecting liquid is used, for instance, water, a hydrocarbon or mercury. The "transducer" is constituted in the known way by a layer of a piezo-electric material metallised on both surfaces, the two surfaces being connected to an alternating voltage generator; under the effect of the electric field created by the voltage generator, the piezo-electric material starts to vibrate, which produces the required ultrasonic beam. If the piezo-electric material is plane, the beam produced is naturally divergent and it can be made to converge by bonding to the piezo-electric material a plano-concave lens made, for instance, of a plastic such as that known under the commerical name of "Araldite". If the piezo-electric material has a concave dome shape, the beam obtained is directly convergent. A mosaic of elementary "transducers" distributed over the surface of the part to be investigated can be used, and in that case, the focusing of the beam can be obtained at the emission or receiving stage; if focused at emission, the different elementary "transducers" are excited with a time lag to produce a spherical wave and the adjustment of the time lag makes it possible to regulate the convergence, orientation and the translation of the focusing axis. If focusing is effected at the receiving stage, each point of the soniferous zone is considered as a secondary transmitter and the received signals received from each one of these secondary transmitters are processed by reconstituting the transmitted wave from a given point of the soniferous zone. One may also use electrodynamic "transducers"; with this technique, a constant magnetic field is applied to the material tested and an electric circulation of Foucault currents created by an external winding, generating a variable field; Lorentz forces are produced thereby in the tested material which are variable from point to point which produces an excitation of the tested material itself and this emission can be focused on a zone of the generating material. The invention is in no way limited to any one transducer generator of ultrasounds. The ultrasounds used are generally of the order of some Mhz and are emitted by wave trains provided at a recurrent frequency which may reach some KHz.

The inclination of the ultrasonic beam in relation to the crack plane is an essential characteristic of the implementation of the invention. If the ultrasonic beam used is perpendicular to the crack plane, the echo received by the receiver does not have any significant maximum at the time the focused point of the beam reaches the crack front. The curve that is obtained is the curve 1 of FIG. 1. If the beam is slightly moved away from the normal to the crack plane (for instance by 10°), a maximum echo will be seen to appear on passing the crack front, which corresponds to the curve 2 of FIG. 1. However, this maximum has a rather low intensity in relation to the echo level obtained on the crack plane without the edge effect. If the inclination in relation to the normal is increased, which corresponds to the curve 3 of FIG. 1, the maximum intensity on passing over the crack front does considerably increase in relation to the echo intensity over the crack plane itself; but the echo level weakens as the angle $\alpha$ (that is to say, the complement of the inclination to the normal) decreases. One is therefore led to choose a compromise, because if the echo is too weak, it is difficult to distinguish it from the background noise. According to the invention, it has been found that this compromise was effective when the angle A was compromised between 10° and 80°.

The advantage of the method in accordance with the invention and of the device allowing to be implemented, is considerable because it is thus possible to define accurately the position of the end of the crack (that is to say, of point $S_o$), at any time whilst previously, this positioning was only possible with considerable inaccuracy. This definition can be obtained irrespective as to whether one is concerned with a part subjected to fatigue test or a part in the course of ductile rupture. Moreover, the invention allows the shape of the crack front to be defined at any time which was completely impossible with the earlier methods.

To render the object of the invention more readily understood, a mode of embodiment represented in the attached drawings will now be described by way of a purely illustrative and non-restrictive example.

In these drawings:

FIG. 1 represents three curves showing the intensity I of the echo received by the receiver in relation to the displacement d of the ultrasonic transducer generator with respect to the test piece investigated, and showing in particular the intensity of the echo at the time the focussed beam passes over the crack front for abscissa $d_o$, the curves 1, 2 and 3 being established respectively for values of angle $\alpha$ of 90, 70 and 5°.

FIG. 2 shows schematically in perspective the end of a standard metallic test piece used for the investigation of fatigue crack growth (cyclic stressing) or the investigation of ductile rupture (increasing monotonic loading);

FIG. 3 shows schematically the test piece of FIG. 1 cut open in plane P of the crack growth, the curve F showing the crack front at a given time of the experiment;

FIG. 4 shows schematically the test piece of FIG. 2 and the orientation of axis A of the ultrasonic beam focused in relation to the said test piece, assuming that the ultrasonic transducer generator is outside the said test piece.

FIG. 5 shows schematically the plane of crack growth of the test piece of FIG. 2 showing therein successive positions of the crack front;

FIG. 6 shows schematically a projection on the plane of the crack growth of the test piece of FIG. 2, of the mode of re-orientation and the transverse displacement of axis A of the focussed ultrasonic beam as one is moving away from the plane of symmetry $P_o$ of the test piece.

FIG. 7 is a representative similar to that of FIG. 6 for a variant of the implementation of the method in accordance with the invention;

FIG. 8 shows schematically a device in accordance with the invention permitting a determination of the tip (or end) of the crack of the shape of the crack front and of its displacement with respect to time.

Referring to the drawings, it will be seen that 4 designates in FIGS. 2 and 8 a steel test piece as a whole intended for the investigation of crack growth under cyclic (fatigue stressing) or of the ductile rupture under increasing monotonic loading. This test piece 4 is intended to be positioned in a traction machine of the known type whose upper jaw 5 (see FIG. 8) is fixed and whose lower jaw is subjected to the force intended to be applied to the test piece by means of a loading device 7. The forces are applied to the test piece along arrows G (see FIG. 2) by means of pins passing through the holes 8. The shape of the test piece is defined in a standard manner; the test piece comprises a cut out 9 which is extended in its median plane by a cut 10 whose bottom is chamfered. When the loading is applied to the test piece, a crack formation occurs and the crack develops in the plane P (see FIG. 3) which is perpendicular to the stresses and constitutes a plane of symmetry for the test piece 4. The test piece 4 comprises a transverse plane of symmetry $P_o$ which is perpendicular to P, the intersection of P and of $P_o$ defining the direction D of the crack propagation. At any given time of the crack growth, the crack front F is a curve, frequently of a parabolic shape as represented in FIGS. 3, 5, 6 and 7. The tip of this curve 5 is a point $S_o$ which constitutes the tip (or end) of the crack in $P_o$. FIG. 5 represents the displacement with respect to time and the variation in shape of the crack front F; it will be seen that the crack front opens out on the outside of the test piece at points whose progression in direction D is not equal to the progression of the tip of the crack; this explains why it is not possible to refer to the external development of the crack to become aware of the state of crack growth of the test piece 4.

In accordance with the method of the invention, the test piece 4 is exposed to an ultrasonic beam designated by 11 in FIG. 3. The beam 11 has its acoustic focal point substantially in plane P. Axis A of the beam 11 forms an angle $\alpha$ with plane P. In accordance with the characteristics of propagation of ultrasound in the various mediums concerned, it is known that in order to obtain an inclination $\alpha$ of axis A inside the test piece in relation to the plane P, the beam must be made to enter the test piece 4 by subjecting its axis to an angle of inclination $\alpha'$ in relation to the face of entry into the test piece 4 (see FIG. 4).

FIG. 8 represents one of the possible devices for generating a focused ultrasonic beam 11. In the device described, a "transducer" 12 is used having a lower concave surface immersed in a tank of water 13 positioned on the upper surface of the test piece 4. The transducer 12 can be a planar transducer associated with a plano-concave lens made from a plastic such as is known under the commercial name of "araldite", or a plano-concave transducer. The active part of the transducer is a pseudo piezo-electric layer constituted by, for instance, a sintered material (barium titanate and barium zirconate; the faces of the pseudo piezoelectric material are metallized and connected to a high frequency electric current generator 14 generating a frequency of the order of some MHz and emitting pulse trains of some KHz. A damping material is disposed at the back of the piezo-electric layer. By way of example, it may be indicated that the piezo-electric layer may have a thickness of approximately 1 mm and form a disc (plane or concave depending on the transducer type) having an external diameter of approximately 20 mm. It is expressly stated that the use of this type of "transducer" is not restrictive and that any other type of "transducer" can be used as long as it allows the application of a focussed ultrasonic beam at a point of plane P.

In accordance with the invention, the transducer 12 is mounted on a manipulating device 15 which is capable of imparting a certain number of movements to the transducer. Firstly, the axis A of the beam 11 can be oriented to form an angle α with plane P comprised between 10° and 80° and preferably approximately to 70°; secondly, the "transducer" 12 can be subjected to rectilinear translational movements, it being possible for these translations to alternate around a reference point and to be either parallel to the direction D, or parallel to the projection of the axis A on the plane P; thirdly, the projection of the axis A on the plane P can be orientated in such a way as to form an adjustable angle with the intersection of planes P and $P_o$; fourthly, the transducer 12 can be subjected to transverse displacement by a translation parallel to plane P. The transducer 12 also has a receiving function and the echo it receives following the emission of a pulse train is directed to a programmer 16 which controls the movements imparted to the transducer 12 by the manipulating device 15. The data relating to the echo intensity and possibly to the transit time are forwarded to a memory device 17, which, depending on the data can send instructions to the programmer 16. The memory device 17 is also connected to a display device 18; the said display being either digital or graphical.

If it is intended to define the position of the tip of the crack $S_o$, in the plane $P_o$, axis A of the beam 11 is brought into the plane $P_o$ and it is subjected to translation until the maximum echo is picked up. The adjustment of the inclination of axis A in relation to the plane P near plane P is effected in such a way that this maximum may be easily discerned (see in this connection the explanations above given with regard to the curves of FIG. 1). When the maximum echo is picked up, the point of intersection of axis A with plane P is located at point $S_o$.

If it is then intended to follow the displacement of the crack front with respect to time, alternating translations in relation to the point of reference constituted by the tip of the crack are imparted to the transducer 12 by the manipulating device 15. As long as the tip of the crack has not been significantly displaced, the reference point is not modified. On the other hand, when there has been a significant displacement of the point in respect of which, the maximum echo is obtained, the displacement of the tip of the crack is recorded in the memory device 17 and the programmer 16 is actuated by the memory device 17 so that the alternating transmission imparted to the transducer 12 should subsequently be undertaken on either side of a new reference point constituted by the new position of the tip of the crack. Thus the displacement of the tip of the crack with respect to time can be followed with a particularly remarkable accuracy, the results being displayed with respect to time on the display device 18.

If one wishes to define the shape of the crack front after the tip of the crack $S_o$ has been positioned, the transducer 12 is subjected to transverse displacement so that the axis of A is moved away from the plane $P_o$ by a value equal to the stage of the displacement, whilst remaining parallel to this plane. One then recommences with subjecting the transducer 12 to a translation parallel to D and the echo maximum is redetermined, which makes it possible to obtain the tip of the crack in the plane perpendicular to P where the axis A is positioned. Thus, the crack front is determined point by point and and simultaneously one calculates the angle of inclination of the tangent with the crack front in relation to the plane passing through A and perpendicular to P: Initially, this angle is 90° and it decreases; when it reaches the value of 75°, axis A is reorientated by a rotation of the transducer actuated by the manipulating device 15 so as to bring it into a plane perpendicular to the tangent to the crack front at the point considered; Axis A is then in a plane Q whose trace in plane P has been designated by Q in FIGS. 6 and 7. The determination of the crack front is then continued by resubjecting the transducer 12 to alternating translations on either side of the reference point constituted by the tip of crack S in the plane Q; these translations can be either parallel to $P_o$ as indicated in FIG. 6, or parallel to Q as indicated in FIG. 7. Then, to continue with the definition of the crack front, the transducer 12 is displaced by a value e, this displacement being effected either perpendicular to plane $P_o$, or parallel to plane Q, according to the situations of FIGS. 6 or 7 respectively.

It will thus be seen that the application of the device in accordance with the invention does not only make it possible to position the tip of the crack accuately and to measure its displacement with respect to time, but also to determine the exact shape of the crack front with accuracy and, of course, the evolution of this shape with respect to time when the crack front is displaced along direction D.

It shall be duly understood that the mode of embodiment described above is in no way restrictive and may give rise to any desirable modifications without thereby departing from the scope of the invention.

We claim:

1. A method for detecting the position of at least one point of a crack front within a part having one of a crack formation and a ductile rupture substantially in a given plane P on either side of a median plane $P_o$ extending perpendicular to said given plane, the method comprising the steps of directing onto the given plane P an incident ultrasonic beam having an axis A, registering the intensity of the echo resulting from diffraction from the given plane P with a receiver device to deduce an evaluation of the position of the tip of the crack or rupture and including the steps of:

measuring the transit time of the ultrasonic wave diffracted by the given plane P to determine the location of the plane P;

subsequently, focusing an incident ultrasonic beam in such a way that the plane P intersects the beam and forms an angle alpha of between approximately 10° and 80° with the axis A of the beam;

orienting the beam so that a plane Q, which is normal to the plane P, passes through the axis A and is substantially perpendicular to the crack front; and displacing the axis A of the beam towards the crack front parallel to the plane P until a maximum echo intensity is registered, the point at which the maximum echo intensity is registered being a point S which is the intersection of the axis A and the plane P and corresponds to the tip of the crack in the plane Q.

2. Method according to claim 1, characterised in that the angle α is comprised between 60° and 75°.

3. Method according to claims 1 or 2, characterised in that the detection is started by bringing the plane Q to be substantially identical with $P_o$.

4. The method as claimed in claim 3, wherein the shape of the crack front is determined, comprising the steps of, after first determining the point S in plane $P_o$, displacing the axis A of the incident beam perpendicularly to the plane $P_o$, to bring said axis into a plane $P_1$ extending parallel to the plane $P_o$, the displacing the axis A of the beam parallel to the plane $P_o$ until a maximum echo intensity is registered thereby determining the position of the tip of the crack in plane $P_1$ and repeating, in steps, the displacement of the axis A of the beam and registering of the maximums to define a tangent T to the crack front which extends at an angle Beta between 5° and 30° with its initial position.

5. The invention as claimed in claim 4, wherein the shape of the crack is further determined, including the steps of moving the axis A so that the plane Q moves through an angle of between Beta and 2Beta, where the angle Beta is initially between 5° and 30°.

6. Method according to claim 5, characterised in that after the reorientation of axis A, A is displaced parallel to $P_o$ and it is displaced transversely perpendicular to $P_o$.

7. Method according to claim 5, characterised in that after the reorientation of the axis A, A is displaced parallel to the intersection of P with the plane Q and it is displaced transversely perpendicular to Q.

8. Method according to one of claim 4, characterised in that $10 \leq \beta \leq 20°$.

9. The method as claimed in claim 1 wherein the displacement along a selected direction D of the tip of the crack is tracked with respect to time, comprising the steps of effecting alternating translation of the axis A parallel to the direction D on either side of the position of the point S and, when a significant variation is detected in the position of the axis A in the echo intensity of the incident beam for the maximum of the intensity of the echo, registering a new position point S' for the tip of the crack, replacing the point S.

10. A device for detecting the position of at least one point of a crack front within a part having one of a crack formation and a ductile rupture substantially in a given plane P on either side of a median plane $P_o$ extending perpendicular to said given plane, the method comprising the steps of directing onto the given plane P an incident ultrasonic beam having an axis A, registering the intensity of the echo resulting from diffraction from the given plane P with a receiver device to deduce an evaluation of the position of the tip of the crack or rupture and including the steps of:

measuring the transit time of the ultrasonic wave diffracted by the given plane P to determine the location of the plane P;

subsequently, focusing an incident ultrasonic beam in such a way that the plane P intersects the beam and forms an angle alpha of between approximately 10° and 80° with the axis A of the beam;

orienting the beam so that a plane Q, which is normal to the plane P, passes through the axis A and is substantially perpendicular to the crack front; and displacing the axis A of the beam towards the crack front parallel to the plane P until a maximum echo intensity is registered, the point at which the maximum echo intensity is registered being a point S which is the intersection of the axis A and the plane P and corresponds to the tip of the crack in the plane Q, said device comprising:

means for fixing the part to be investigated, means for imparting mechanical stresses to the part to cause the production, substantially in a plane P of the part, a crack formation or a ductile rupture, at least one ultrasonic generating means for providing a focused beam incident on the part and at least one receiving means for registering the intensity of the echo of the incident beam from the part, said generating means providing the beam so that the beam intersects the plane P and forms with the axis A of the beam an angle alpha of between approximately 10° and 80°, said device further including means for moving the axis A of the beam about the perpendicular plane Q, means for translating the axis A of the beam in a first direction parallel to the plane P and in a second direction also parallel to the plane P.

11. Device according to claim 10, characterised in that $60 < \alpha < 75°$.

12. Device according to one of claims 10 or 11, characterized in that the means for moving the axis A are controlled by a control means making it possible to ensure a continuous translation until a maximum echo is registered by the receiving means followed by a return movement, for which the receiver registers a maximum echo, the displacement of the said reference point with respect to time being recorded by a recording means.

13. Device according to claim 12, characterised in that the means for the transverse displacement of the axis A produce a translation of the said axis along a second direction which is perpendicular to the first direction.

14. Device according to claim 12, characterised in that the means for the translational displacement of the axis A ensure a translation over a single first direction positioned in relation to the fixing means for the part.

15. A device according to claim 12 characterised in that the generating means used is a plane transducer focused by a plano-concave lens.

16. Device according to chaim 12, characterised in that the means for the orientation and translational shift of the axis A are, controlled automatically by a program from the detection of the tip of the crack $S_o$ situated in the median plane $P_o$ on either side whereof the crack front is disposed, the geometrical position of at least part of the crack front and its displacement with respect to time, being stored by computer with a view to a digital or graphical read-out.

17. Device as claimed in claim 12 wherein said generating means is a concave transducer.

18. Device as claimed in claim 12 wherein said generating means is a mosaic of elementary transducers focused electronically.

19. Device as claimed in claim 12 wherein said generating means is an electrodynamic focusing transducer.

* * * * *